United States Patent
Penna et al.

(10) Patent No.: US 10,342,629 B2
(45) Date of Patent: *Jul. 9, 2019

(54) SHIPPING MEMBER FOR LOADING UNIT

(71) Applicant: Covidien LP, Mansfield, MA (US)

(72) Inventors: Christopher Penna, Guilford, CT (US); Patrick Mozdzierz, Glastonbury, CT (US); Paul A. Scirica, Huntington, CT (US); Justin Williams, Southbury, CT (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/034,916

(22) Filed: Jul. 13, 2018

(65) Prior Publication Data

US 2018/0318030 A1 Nov. 8, 2018

Related U.S. Application Data

(63) Continuation of application No. 15/429,350, filed on Feb. 10, 2017, now Pat. No. 10,022,198, which is a
(Continued)

(51) Int. Cl.
*A61B 50/30* (2016.01)
*A61B 17/068* (2006.01)
(Continued)

(52) U.S. Cl.
CPC ............ *A61B 50/30* (2016.02); *A61B 17/068* (2013.01); *A61B 17/1155* (2013.01);
(Continued)

(58) Field of Classification Search
CPC ... A61B 50/30; A61B 17/068; A61B 17/1155; A61B 2090/0801; A61B 17/064; A61B 2017/00473; A61B 2017/07271
(Continued)

(56) References Cited

U.S. PATENT DOCUMENTS

| 4,078,696 A | 3/1978 | Crisci |
| 4,505,272 A | 3/1985 | Utyamyshev et al. |

(Continued)

FOREIGN PATENT DOCUMENTS

| CN | 102579096 A | 7/2012 |
| DE | 102007037593 A1 | 2/2009 |

(Continued)

OTHER PUBLICATIONS

European Office Action dated Sep. 21, 2018, issued in EP Appln. No. 14199690.
(Continued)

*Primary Examiner* — Michelle Lopez

(57) ABSTRACT

A shipping member for selective attachment to a replaceable loading unit is provided. The shipping member includes an annular extension configured for selective engagement with a loading unit and configured to prevent movement of a knife assembly of the loading unit. The shipping member further includes first and second legs configured to prevent movement of a staple pusher assembly. The shipping member also includes a staple retaining surface configured to retain staples within a staple cartridge of the loading unit.

18 Claims, 13 Drawing Sheets

Related U.S. Application Data continuation of application No. 14/149,355, filed on Jan. 7, 2014, now Pat. No. 9,579,099.

(51) Int. Cl.
*A61B 17/115* (2006.01)
*A61B 17/00* (2006.01)
*A61B 17/072* (2006.01)
*A61B 90/00* (2016.01)
*A61B 17/064* (2006.01)

(52) U.S. Cl.
CPC ... *A61B 17/064* (2013.01); *A61B 2017/00473* (2013.01); *A61B 2017/07271* (2013.01); *A61B 2090/038* (2016.02); *A61B 2090/0801* (2016.02)

(58) Field of Classification Search
USPC .......................................... 227/175.1, 176.1
See application file for complete search history.

(56) References Cited

U.S. PATENT DOCUMENTS

| | | | |
|---|---|---|---|
| 5,669,918 A | 9/1997 | Balazs et al. | |
| 5,836,503 A | 11/1998 | Ehrenfels et al. | |
| 6,050,472 A * | 4/2000 | Shibata | A61B 17/115 227/175.2 |
| 7,182,239 B1 | 2/2007 | Myers | |
| 8,006,701 B2 | 8/2011 | Bilotti et al. | |
| 8,118,206 B2 | 2/2012 | Zand et al. | |
| 9,579,099 B2 * | 2/2017 | Penna | A61B 17/068 |
| 9,750,503 B2 * | 9/2017 | Milliman | A61B 90/98 |
| 10,022,198 B2 * | 7/2018 | Penna | A61B 17/068 |
| 2002/0020732 A1 | 2/2002 | Adams et al. | |
| 2009/0065387 A1 | 3/2009 | Bammerlin et al. | |
| 2009/0082777 A1 | 3/2009 | Milliman et al. | |

FOREIGN PATENT DOCUMENTS

| | | |
|---|---|---|
| EP | 0724864 A1 | 8/1996 |
| EP | 2462875 A2 | 6/2012 |
| EP | 2604195 A1 | 6/2013 |
| EP | 2604197 A2 | 6/2013 |
| EP | 2886071 A1 | 6/2015 |
| WO | 03079909 A2 | 10/2003 |
| WO | 2013026402 A1 | 2/2013 |
| WO | 2013154508 A1 | 10/2013 |

OTHER PUBLICATIONS

Australian Examination Report dated Sep. 26, 2018, cited in AU Appln. No. 2014256365.
European Search Report EP 14199690 dated May 15, 2015.
Chinese Office Action dated Mar. 27, 2018 issued in CN Application No. 2014108434973.
Australian Office Action dated Jan. 28, 2019, issued in AU Appln. No. 2014256365.

* cited by examiner

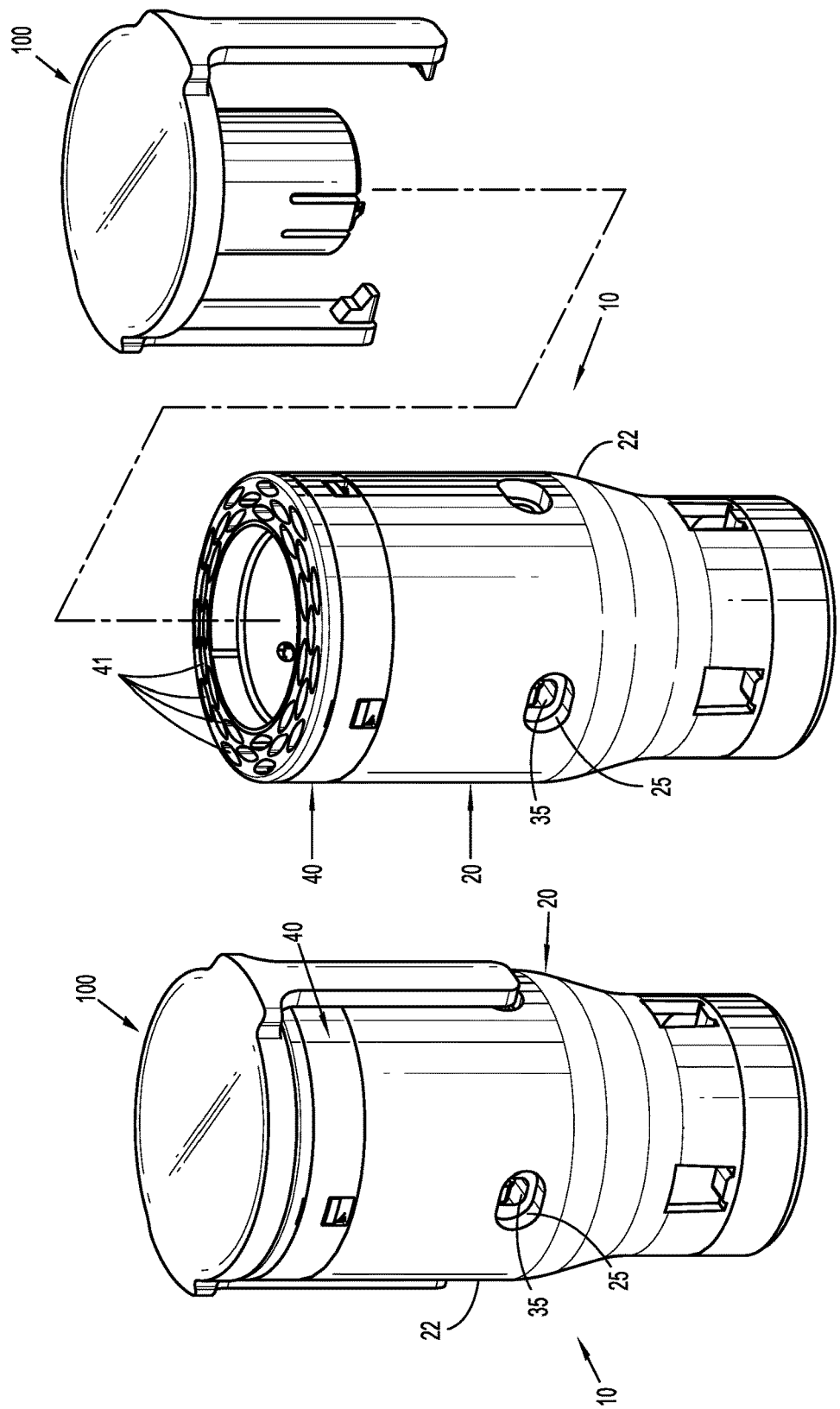

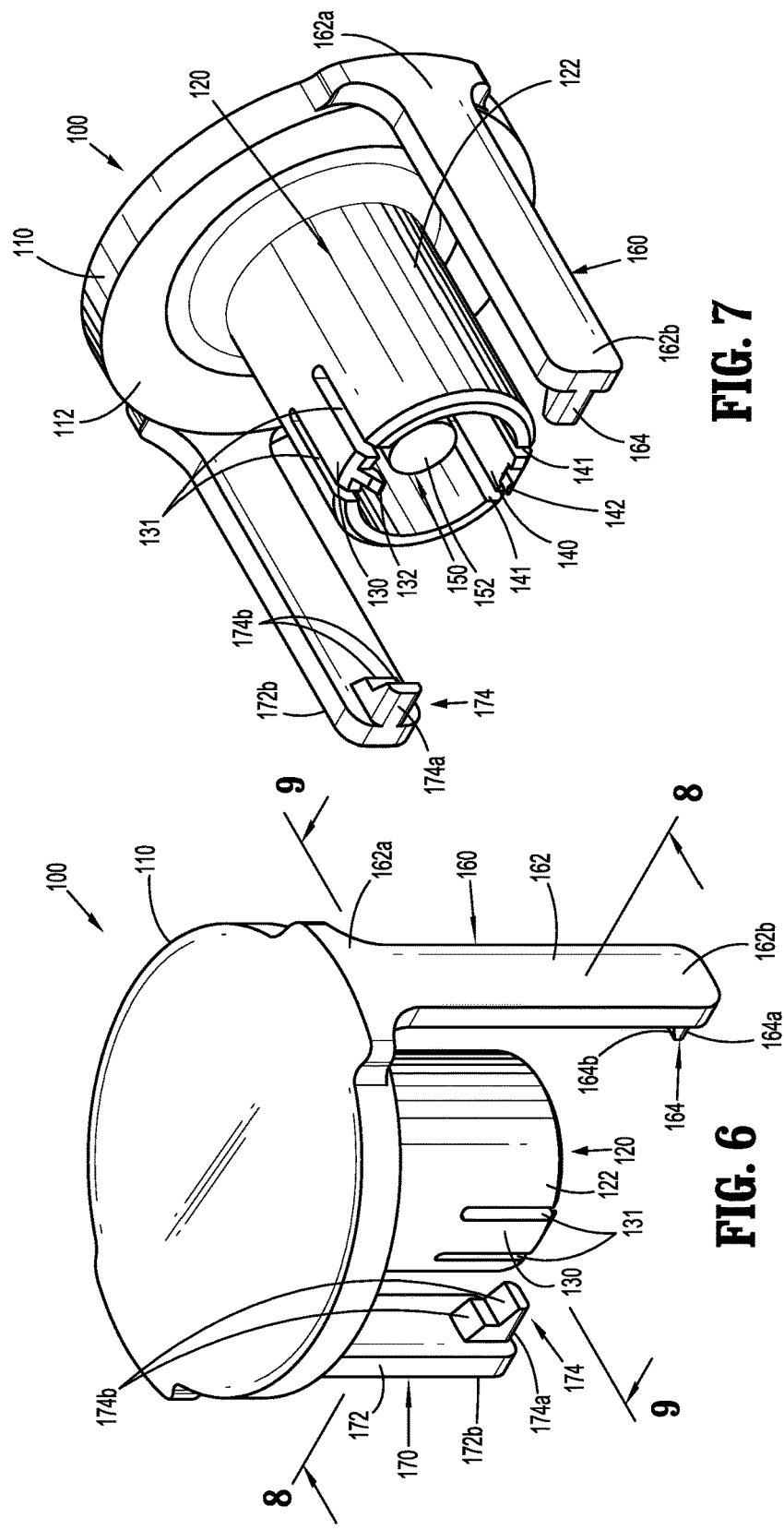

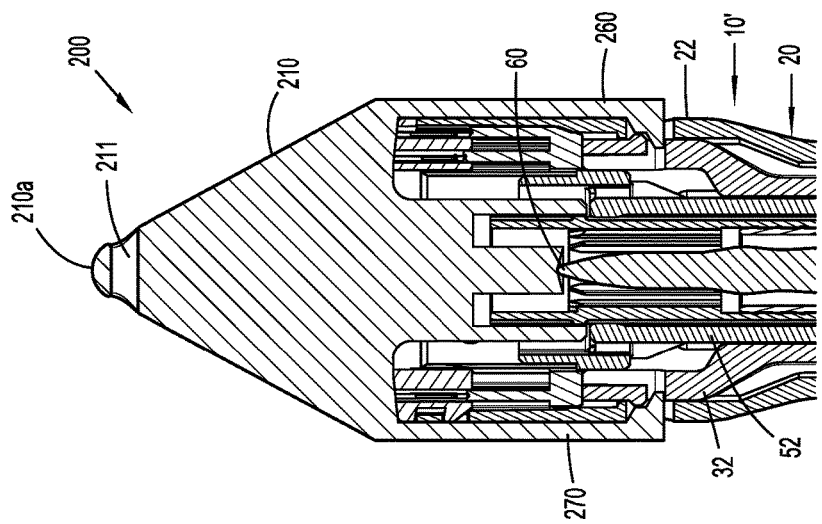
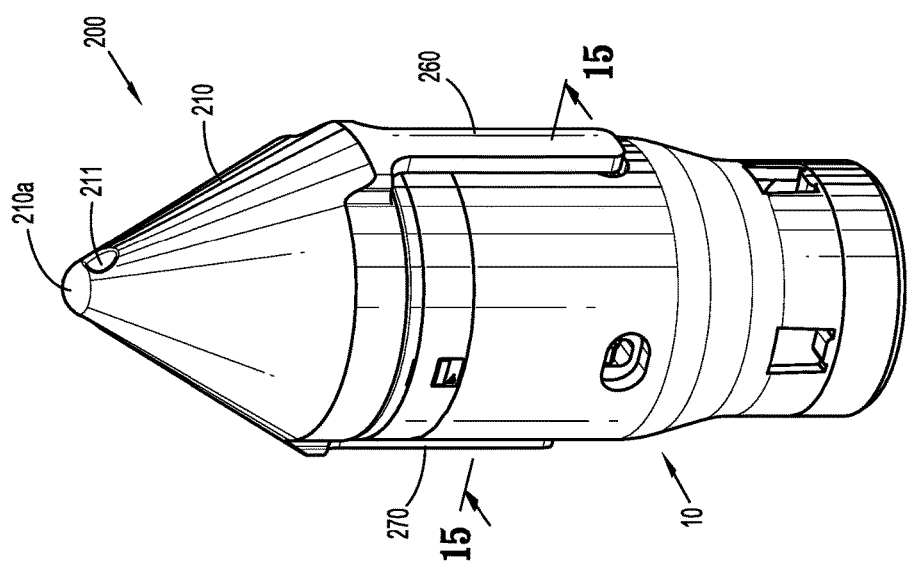

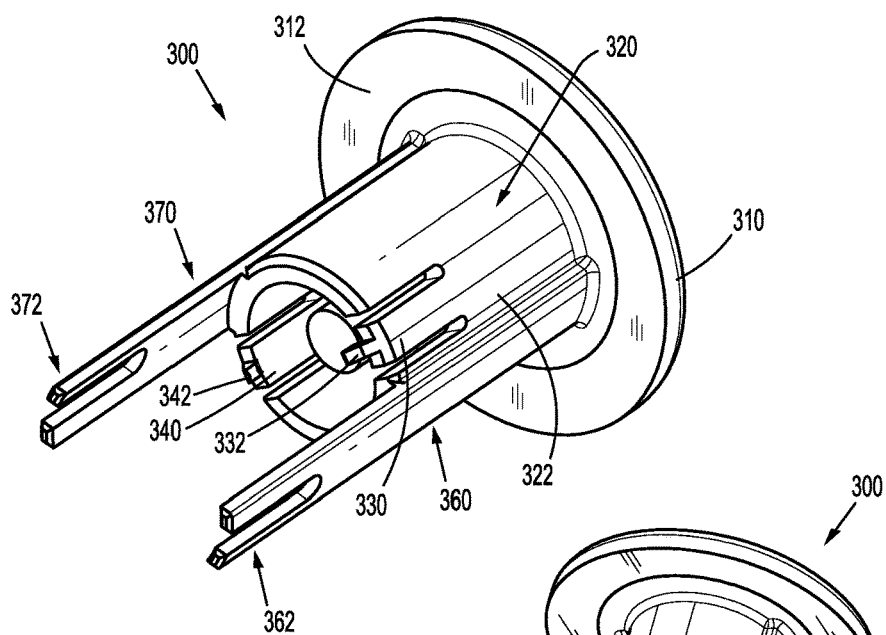
FIG. 18
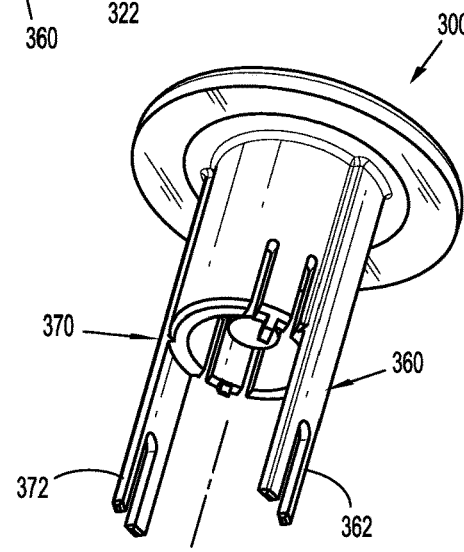
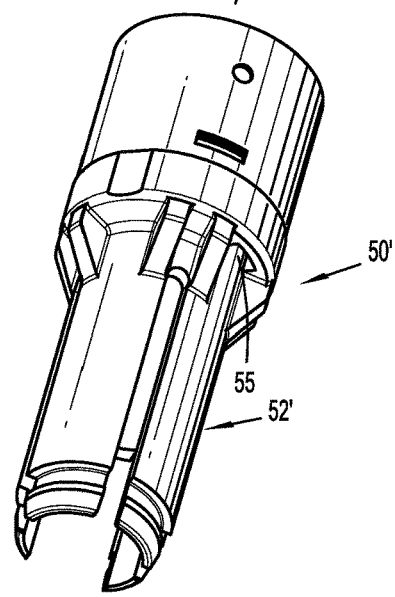
FIG. 19

SHIPPING MEMBER FOR LOADING UNIT

CROSS-REFERENCE TO RELATED APPLICATIONS

This is a continuation application of U.S. patent application Ser. No. 15/429,350, filed Feb. 10, 2017, which is a continuation application and claims the benefit of and priority to U.S. patent application Ser. No. 14/149,355 filed Jan. 7, 2014, now (U.S. Pat. No. 9,579,099), the entire disclosure of which is incorporated by reference herein.

BACKGROUND

Technical Field

The present disclosure relates to surgical stapling devices including replaceable loading units. More particularly, the present disclosure relates to shipping members for selective attachment to the loading units.

Background of Related Art

Surgical devices for applying surgical fasteners to tissue are well known. Endoscopic surgical devices for applying staples, clips, or other fasteners include an actuation unit, i.e., a handle assembly for actuating the device and a shaft for endoscopic access, and a tool assembly disposed at a distal end of the shaft. Certain of these devices are designed for use with replaceable loading units which include the tool assembly and house the staples or fasteners. The replaceable loading units may include staples of various sizes and the staples may be arranged in one or more configurations. After firing the stapler with a replaceable loading unit, the user may remove the empty loading unit, select and attach to the stapler another loading unit having staples of the same or different size and the same or different staple arrangement, and fire the stapler again. This process may be performed repeatedly during a surgical procedure.

Many loading units typically include a staple cartridge, a staple pusher assembly, and, optionally, a knife assembly. Loading units including a knife assembly have the benefit of providing a new knife with each loading unit. The staple pusher and knife assemblies generally include one or more movable parts positioned to engage one or more drive members of the actuation unit. If the moving parts are not properly retained in a proper position prior to and during attachment of the loading unit to the actuation unit, the loading unit may not properly engage the actuation unit, and thus, may not function properly. Some loading units are provided with automatic locking systems which block movement of the components of the loading unit prior to attachment of the loading unit to the actuation unit and allow free movement of the movable parts of the loading unit once the loading unit has been properly positioned on the actuation unit. However, these automatic locking systems do not address the retention of the staples within the staple cartridge prior to activation of the loading unit. Further, these automatic locking systems are not configured to facilitate positioning of the loading unit within tissue.

Therefore, it would be beneficial to have a shipping member configured to maintain the movable parts of the loading unit. It would be further beneficial if the shipping member operates to maintain the staples within the staple cartridge and/or facilitates positioning of the loading unit within tissue.

SUMMARY

Accordingly, a shipping member is provided. The shipping member includes a base having a staple retaining surface, an annular extension extending proximally from the base and including first and second arms and an ejection post, and first and second legs extending proximally from the base and each including radially inward extending tabs projecting therefrom. Each of the first and second arms includes a snap feature projecting therefrom.

In one embodiment, the first and second legs are radially spaced from the annular extension. As such, the staple retaining surface is disposed between the annular extension and the first and second legs. Alternatively, the first and second legs may be integrally formed with the annular extension. In this manner, the staple retaining surface is disposed radially outward of the first and second legs. The staple retaining surface may be annular. The snap feature of the first and second arms may extend radially inward. The base may include a conical shape. The base may include a throughhole formed therein. The tabs of the first and second legs may include a flat proximal facing surface and an inclined distal facing surface.

Also provided is a loading unit including a housing, a staple pusher assembly operably retained within the housing, a knife assembly operably retained within the housing, a cartridge assembly disposed on a distal end of the housing and including a plurality of staples, and a shipping member selectively engaged to the housing. The shipping member may include an inner surface disposed adjacent the staple cartridge for maintaining the plurality of staples within the staple cartridge, an annular extension configured to selectively engage the knife assembly, the annular extension including first and second arms configured to frictionally engage the housing, and first and second legs each including a tab extending therefrom configured to selectively engage the staple pusher assembly.

In embodiments, the tab of the first and second legs may include a flat proximal facing surface configured to selectively engage the staple pusher assembly. The housing may include an outer cylindrical portion defining a plurality of openings. The tabs of the first and second legs of the shipping member may be configured for receipt through the openings in the outer cylindrical portion. The first and second arms of the extension may each include a snap feature configured to engage a ridge formed on an inner cylindrical portion of the housing. The annular extension may further includes an ejection post including a proximal facing surface.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein:

FIG. 1 is a perspective side view of a shipping member according to an embodiment of the present disclosure disposed on a replaceable loading unit;

FIG. 2 is a perspective side view of the shipping member shown in FIG. 1 separated from the loading unit shown in FIG. 1;

FIG. 6 is a perspective side view of the shipping member shown in FIG. 1;

FIG. 7 is a perspective bottom view of the shipping member shown in FIG. 6;

FIG. 14 is a perspective side view of the shipping member shown in FIG. 12 selectively disposed on a loading unit;

FIG. 15 is a cross-sectional view of the shipping member and loading unit taken along line 15-15 shown in FIG. 14;

FIG. 18 is a perspective end view of the shipping member shown in FIG. 16;

FIG. 19 is a perspective side view of the shipping member shown in FIG. 16 and a knife assembly of the loading unit shown in FIG. 16, with the parts separated;

DETAILED DESCRIPTION

Figure 3:
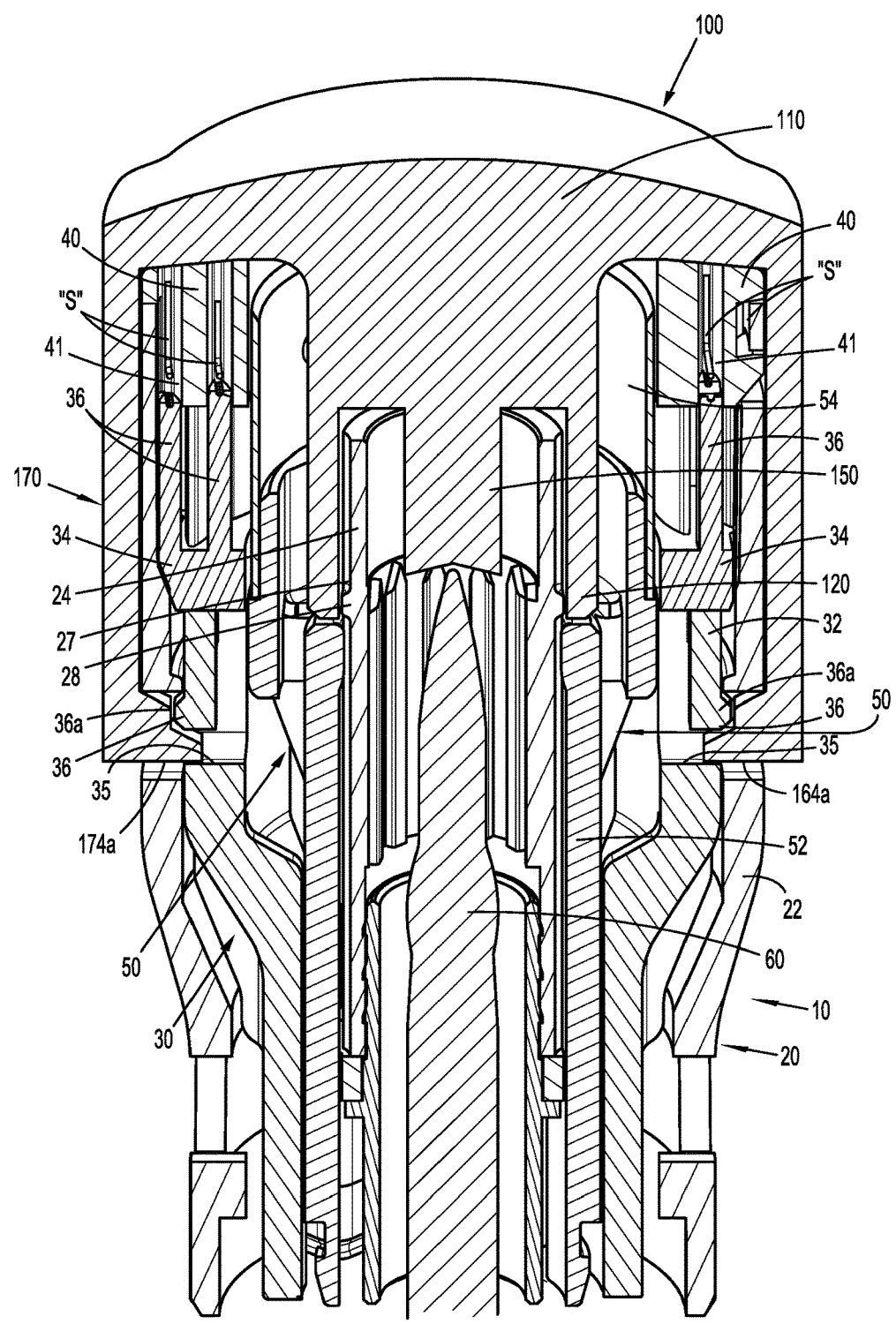
FIG. 3 is a cross-section side view of the loading unit shown in FIG. 1.

Embodiments of the presently disclosed shipping member will now be described in detail with reference to the drawings in which like reference numerals designate identical or corresponding elements in each of the several views. As is common in the art, the term "proximal" refers to that part or component closer to the user or operator, i.e. surgeon or clinician, while the term "distal" refers to that part or component further away from the user.

With reference now to FIGS. 1-3, a shipping member according to an embodiment of the present disclosure is shown generally as shipping cap 100. Shipping cap 100 is configured to be selectively received on a distal end of a loading unit 10 and operates to maintain staples "S" (FIG. 3) within a staple cartridge 40 disposed on a distal end of loading unit 10. Shipping cap 100 also operates to prevent premature advancement of a staple pusher assembly 30 (FIG. 3) and a knife assembly 50 (FIG. 3) prior to and during attachment of loading unit 10 to an actuation unit (not shown) of a stapling device (not shown) or an adapter assembly (not shown) that is connected to the actuation unit of the stapling device.

With reference to now to FIGS. 2-5, an embodiment of a replaceable loading unit suitable for use with shipping cap 100 is shown generally as loading unit 10. Although shown and described for use with loading unit 10, it is envisioned that the aspects of the present disclosure may be modified for use with loading units having other configurations. Loading unit 10 is configured to be selectively received on a distal end of a shaft (not shown) of an actuation unit (not shown) of a stapling device (not shown), or an adapter assembly (not shown) that is configured to interconnect loading unit 10 with the stapling device. Although envisioned for use with a powered actuation unit (not shown), loading unit 10 may be modified for use with a manually actuated actuation unit (not shown). Loading unit 10 will only be described to the extent necessary to fully disclose the aspects of the present disclosure. For a more detail description of an exemplary loading unit, please refer to commonly owned U.S. Patent Application Publication No. 2013/0181035, the content of which is incorporated by reference herein in its entirety.

Figure 5:
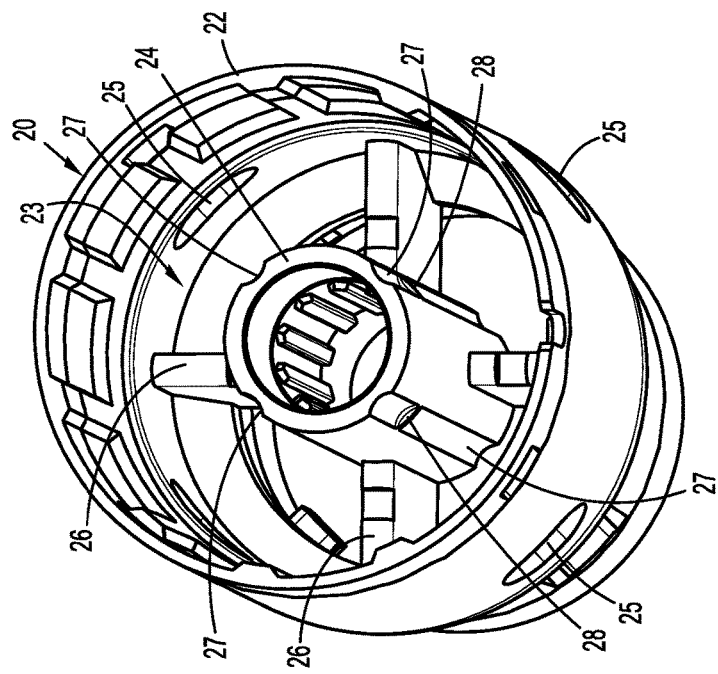
FIG. 5 is perspective top view of the housing of the loading unit shown in FIG. 1.

Briefly, loading unit 10 includes a housing 20, a staple pusher assembly 30, a staple cartridge 40, and a knife assembly 50 (FIG. 3). With particular reference to FIG. 5, housing 20 of loading unit 10 includes an outer cylindrical portion 22, an inner cylindrical portion 24, and a plurality of radially extending supports or ribs 26 extending between and interconnecting inner cylindrical portion 24 and outer cylindrical portion 22. A proximal end of housing 20 is configured for selective connection to an actuation unit (not shown). Inner cylindrical portion 24 and outer cylindrical portion 22 of housing 20 are coaxial and define a recess 23 therebetween configured to operably receive staple pusher assembly 30 (FIG. 3) and knife assembly 50 (FIG. 3). Outer cylindrical portion 22 defines a plurality of openings 25. As will be discussed in further detail below, openings 25 in outer cylindrical portion 22 are configured to selectively receive a portion of shipping cap 100. Although shown including four (4) openings 25, it is envisioned that outer cylindrical portion 22 may define any number of openings 25. Inner cylindrical portion 24 defines longitudinal grooves 27, each including a ridge 28. Grooves 27 correspond in number and location to openings 25 formed in outer cylindrical portion 22. As will be described in further detail below, ridges 28 facilitate selective engagement of shipping cap 100 with loading unit 10.

Figure 4:
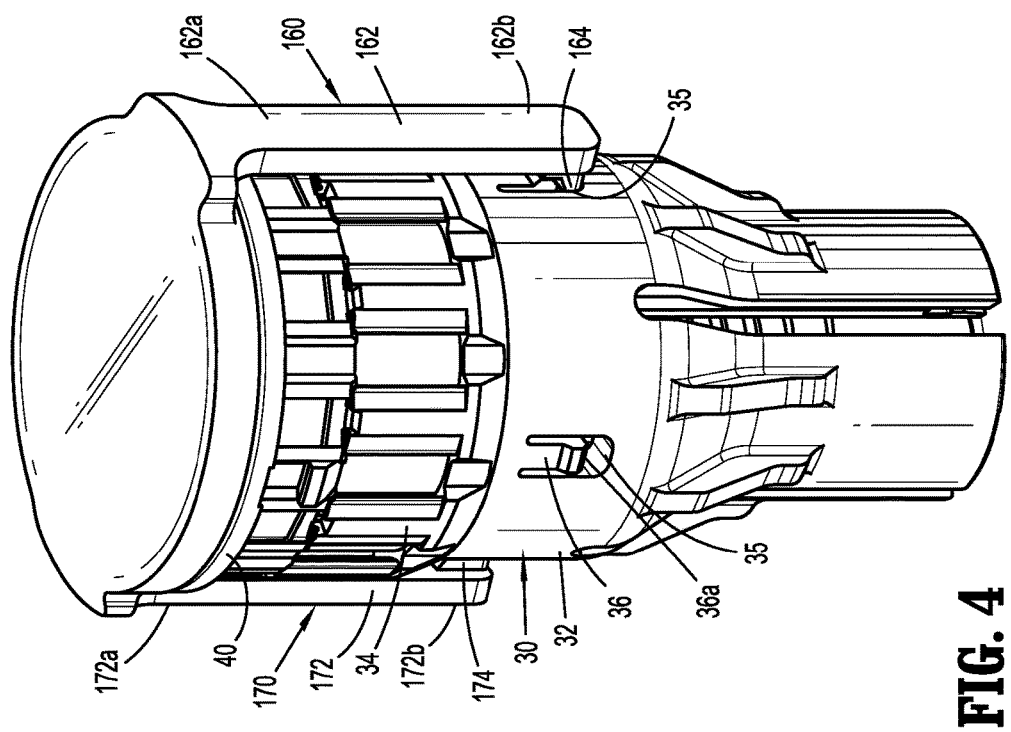
FIG. 4 is a perspective side view of the shipping member and loading unit shown in FIG. 1 with the housing of the loading unit removed.

With continued reference to FIGS. 2-4, staple pusher assembly 30 includes a pusher adapter 32 and a pusher 34. Pusher adapter 32 of staple pusher assembly 30 defines a plurality of openings 35 and includes a finger 36 extending proximally within each of openings 35. Openings 35 and fingers 36 correspond in number and location to openings 25 formed in outer cylindrical portion 22 of housing 20. When pusher adapter 32 is in a proximal or pre-fired position, radially outward extending tabs 36a formed on each of fingers 36 are received within openings 25 formed in outer cylindrical portion 22 and engage outer cylindrical portion 22 to selectively secure pusher adapter 32 in the pre-fired position. During a stapling stroke, a drive mechanism (not shown) of the actuation unit (not shown), applies a force to pusher adapter 32 to disengage tabs 36a from cylindrical portion 22 and causes distal advancement of pusher 34. Pusher 34 includes a plurality of pusher members 38 (FIG. 3) aligned with staples "S" received within staple pockets 41 of staple cartridge 40. Advancement of pusher 34 relative to staple cartridge 40 causes ejection of staples "S" from staple cartridge 40. Knife assembly 50 (FIG. 3) includes a knife carrier 52 and a circular knife 54. Distal advancement of carrier 52 advances circular knife 54, to cause the cutting of tissue (not shown) disposed adjacent to staple cartridge 40 and within the staple line of staple cartridge 40.

Turning now to FIGS. 6-9, shipping cap 100 includes a base 110, an annular extension or stem 120 extending proximally from base 110, and first and second legs 160, 170 radially spaced from annular extension 120 and extending proximally from base 110. Although shown as being of one-piece construction, i.e., integrally or monolithically formed, it is envisioned that any or all of base 110, annular extension 120, and first and second legs 160, 170 may be independently formed and secured together with adhesive, welding, or in any other suitable manner.

As shown, base 110 includes a substantially flat or planar body having a circular shape. Although shown having a circular shape, it is envisioned that base 110 may include any shape corresponding to the cross-sectional shape of loading unit 10 (FIG. 1). It is further envisioned that base 110 may be configured to facilitate removal of shipping cap 100 from loading unit 10. A staple retaining surface 112 (FIG. 8) of base 110 is formed between annular extension 120 and first and second legs 160, 170 and is configured to abut staple cartridge 40 of loading unit 10 when shipping cap 100 is received on the distal end of loading unit 10 to retain staples "S" within staple pockets 41 of staple cartridge 40 during shipment and attachment of loading unit 10 to an actuation unit (not shown) of the stapling device (not shown). Although shown as being annular to correspond with the shape of staple cartridge 40, it is envisioned that staple retaining surface 112 may be modified to correspond with staple cartridges of other configurations.

With reference still to FIGS. 6-9, annular extension 120 of shipping cap 100 includes a cylindrical body 122, first and second arms 130, 140, and an ejection post 150. First and second arms 130, 140 are formed as an integral part of cylindrical body 122 and ejection post 150 extends proximally within cylindrical body 122. As shown, annular extension 120 is formed coaxial with base 110. As will be discussed in further detail below, annular extension 120 is configured to be selectively received within a distal end of housing 20 of loading unit 10 between outer and inner cylindrical portions 22, 24 (FIG. 5) of housing 20 and about a distal end of inner cylindrical portion 24 of housing 20.

Each of first and second arms 130, 140 are formed by a pair of cutouts 131, 141 (FIGS. 6 and 7) formed in annular extension 120. Each of first and second arms 130, 140 is configured to be flexed radially outward relative to cylindrical body 122 of annular extension 120 and includes a snap feature 132, 142, respectively, formed on respective proximal ends thereof. Snap features 132, 142 project radially inward from respective first and second internal arms 130, 140. Snap features 132, 142 are configured to engage annular ridges 28 (FIG. 5) formed within longitudinal grooves 27 defined by inner cylindrical portion 24 of housing 20 of loading unit 10. Ejection post 150 is coaxially disposed within annular extension 120 and includes a proximal end 152 configured to be engaged by a retaining pin 60 (FIG. 3) of an actuation unit (not shown) to facilitate detachment of shipping cap 100 from loading unit 10. Proximal end 152 may have a concave profile.

Figure 8:
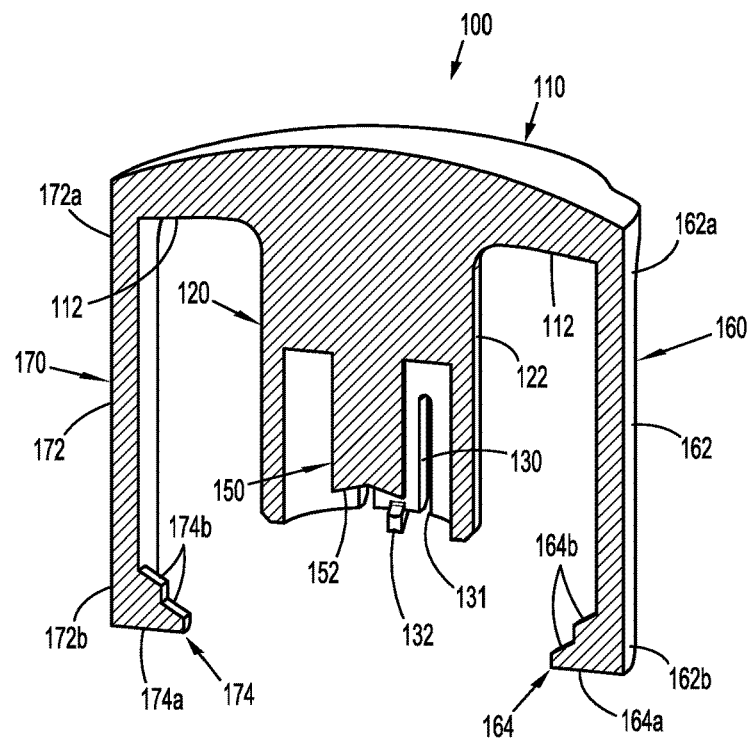
FIG. 8 is a cross-sectional side view taken along line 8-8 shown in FIG. 6.
Figure 9:
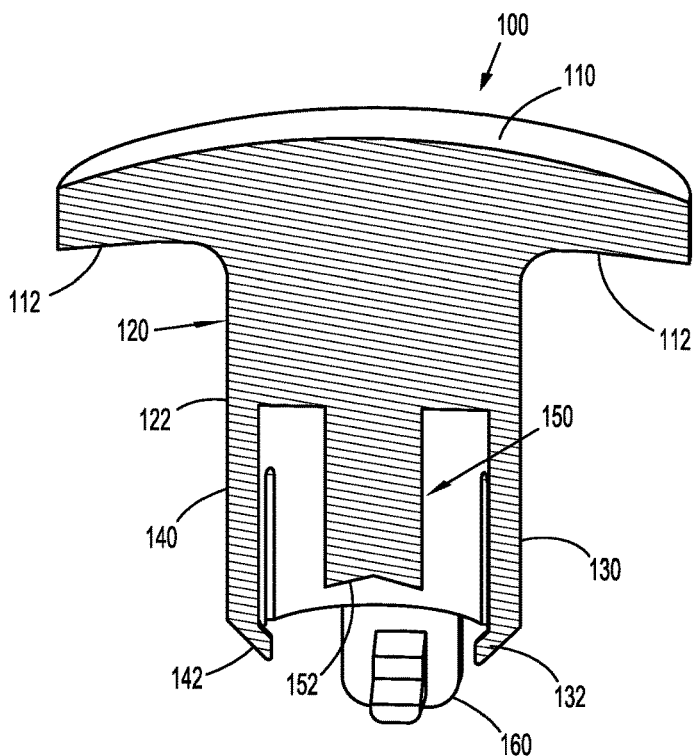
FIG. 9 is a cross-sectional side view taken along line 9-9 shown in FIG. 6.

With reference still to FIGS. 6-8, first and second legs 160, 170 of shipping cap 100 extend proximally from opposite sides of base 110 and are configured to selectively engage housing 20 of loading unit 10 (FIG. 4). Although shown having two legs 160, 170, it is envisioned that shipping cap 100 may include more than two legs. First and second legs 160, 170 are substantially identical and each includes an elongate portion 162, 172, respectively. A distal end 162a, 172a of elongate portion 162, 172, respectively, is connected to base 110. As will be described in further detail below, first and second legs 160, 170 are configured to flex radially outward relative to base 110. Although shown being integrally formed with base 110, it is envisioned that first and second legs 160, 170 may be secured to base 110 in any suitable manner.

A second end 162b, 172b of elongate portion 162, 172, respectively, each include a tab or engagement member 164, 174. Tabs 164, 174 extend radially inward from respective second ends 162b, 172b of elongate portions 162, 172, respectively, and are configured to be received through openings 25 formed in outer cylindrical portion 22 of housing 20 of loading unit 10 (FIG. 3) and within openings 35 formed in pusher adapter 32 of staple pusher assembly 30 (FIG. 3). Engagement of tabs 164, 174 with pusher adapter 32 prevents distal movement of pusher adapter 32. In particular, tabs 164, 174 include a flat proximal facing surface 164a, 174a configured to engage pusher adapter 32. Inclined or wedge shaped distal facing surfaces 164b, 174b of tabs 164, 174, respectively, are configured to facilitate withdrawal of respective tabs 164, 174 from within openings 25 in outer cylindrical portion 122 of housing 20. As noted above, elongate portions 162, 172 of respective first and second legs 160, 170 are configured to flex radially outwardly relative to base 110 to facilitate positioning of tabs 164, 174 within openings 25 formed in outer cylindrical portion 122 of housing 20 and to facilitate withdrawal of tabs 164, 174 from within openings 25 formed in outer cylindrical portion 122 of housing 20.

Figure 11:
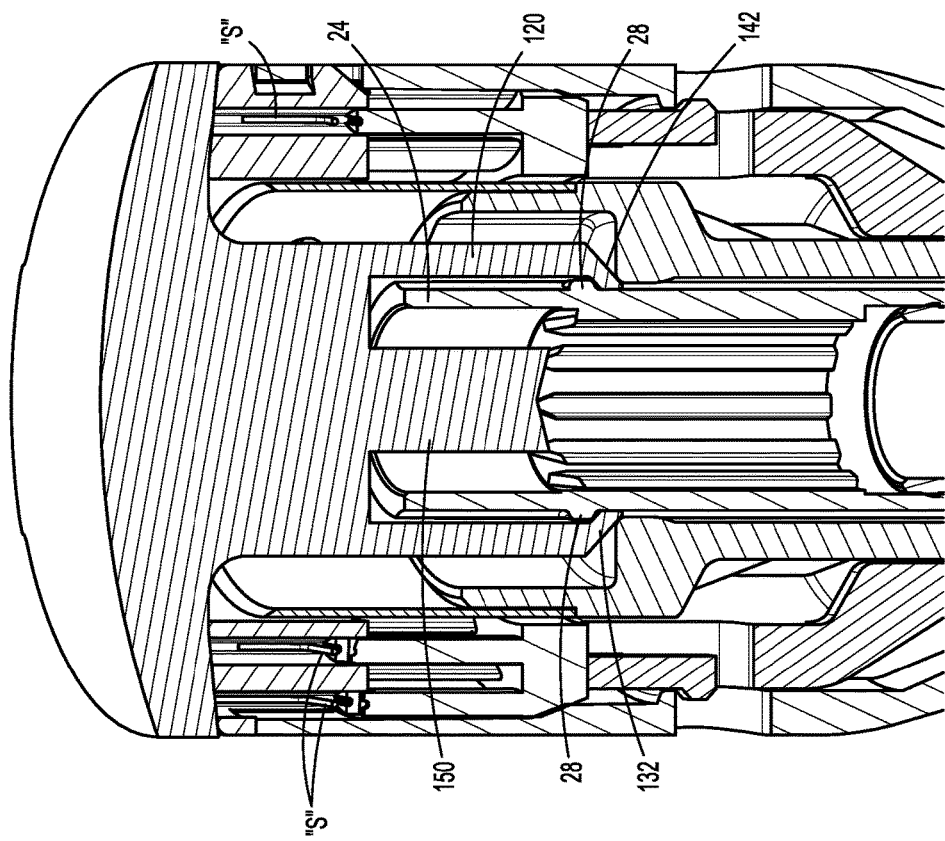
FIG. 11 is a perspective, cross-sectional side view of the shipping member and loading unit shown in FIG. 1.
Figure 10:
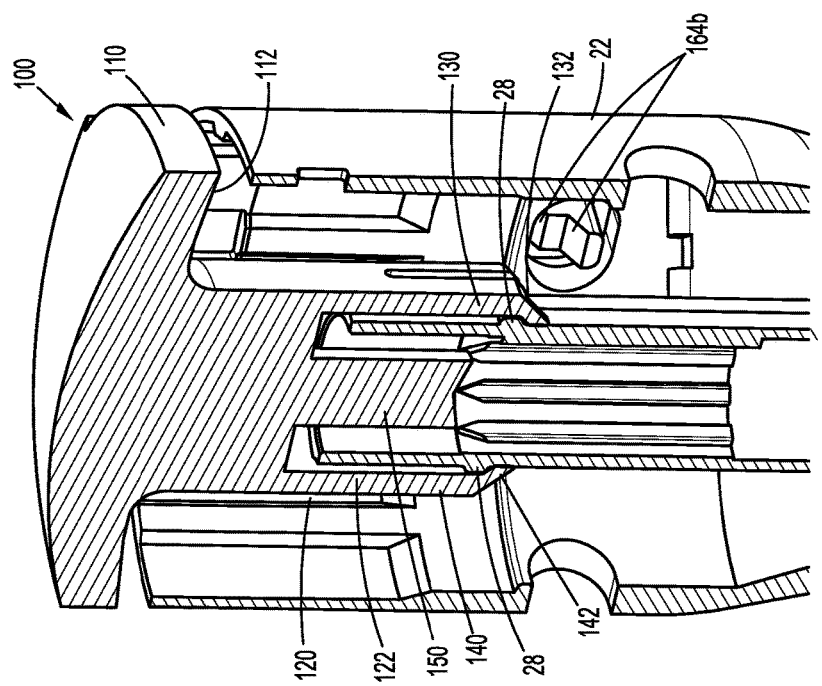
FIG. 10 is a perspective, cross-sectional side view of the shipping member and loading unit shown in FIG. 1, with the staple pusher assembly and knife assembly removed.
Figure 12:
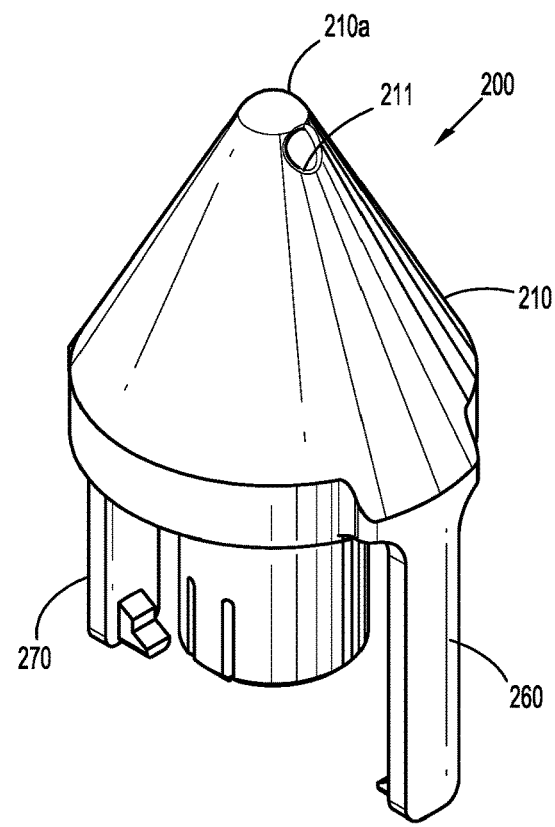
FIG. 12 is perspective side view of a shipping member according to an alternative embodiment of the present disclosure.
Figure 13:
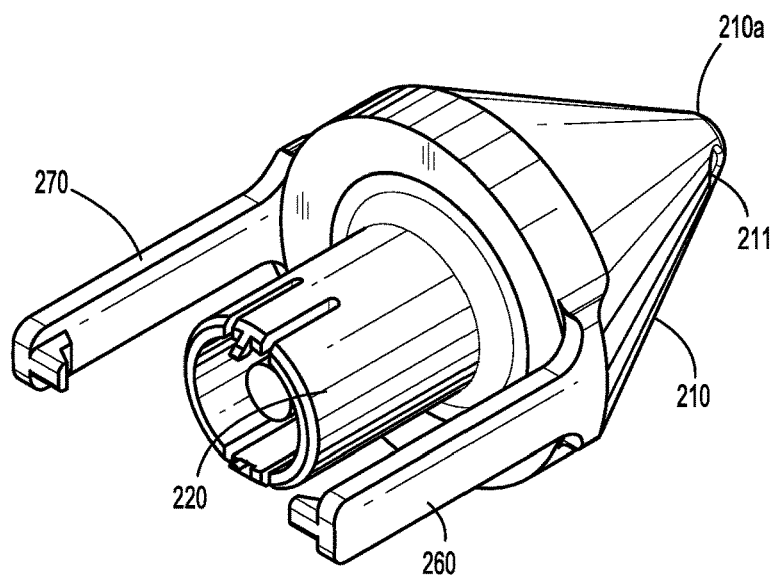
FIG. 13 is a perspective bottom view of the shipping member shown in FIG. 12.

With reference now to FIGS. 10 and 11, shipping cap 100 is shown selectively received or attached on the distal end of loading unit 10. Shipping cap 100 is received on the distal end of loading unit 10 through frictional engagement of shipping cap 100 with loading unit 10. In particular, shipping cap 100 is positioned relative to loading unit 10 such that first and second legs 160, 170 align with openings 25 formed in outer cylindrical portion 22 of housing 20 of loading unit 10 and annular extension 120 aligns with inner cylindrical portion 24 of housing 20 of loading unit 10. First and second legs 160, 170 are then flexed radially outward to permit first and second legs to be received about outer cylindrical portion 22 of housing 20 as shipping cap 100 is approximated towards loading unit 10 such that annular extension 120 is received within the distal end of loading unit 10.

Alignment of first and second legs 160, 170 of shipping cap 100 with openings 25 formed in outer cylindrical portion 22 of housing 20 of loading unit 10 ensures that snap features 132, 142 formed on first and second arms 130, 140 of annular extension 120 align with longitudinal grooves 27 formed on inner cylindrical portion 24 of housing 20 of loading unit 10. Continued approximation of shipping cap 100 towards loading unit 10 causes tabs 164, 174 formed on first and second legs 160, 170, respectively, of shipping cap 100 to be received within openings 25 formed in outer cylindrical portion 22 of housing 20 of loading unit 10 and causes snap features 132, 142 formed on first and second arms 130, 140 of annular extension 120 of shipping cap 100 to engage ridges 28 formed on inner cylindrical portion 24 of housing 20 of loading unit 10.

When shipping cap 100 is received on the distal end of loading unit 10, annular extension 120 of shipping cap 100 is received within housing 20 of loading unit 10 and about inner cylindrical portion 24 of housing 20. In particular, annular extension 120 is disposed about inner cylindrical portion 24 of housing 20 of loading unit 10; inner surface 112 of base 110 of shipping cap 100 is disposed adjacent staple pockets 41 of staple cartridge 40 of loading unit 10; ejection post 150 of annular extension 120 is received within inner cylindrical portion 24 of housing 20 of loading unit 10; annular extension 120 engages knife carrier 52 (FIG. 3) of loading unit 10; and, snap features 132, 142 formed on respective first and second arms 130, 140 of annular extension 120 engage ridges 28 formed on inner cylindrical portion 24 of housing 20 of loading unit 10.

The positioning of inner surface 112 of base 110 adjacent staple pockets 41 of staple cartridge 40 ensures that staples "S" (FIG. 11) are maintained within staple pockets 41 of staple cartridge 40 of loading unit 10, thereby preventing staples "S" from being dislodged during shipping and attachment of loading unit 10 to an actuation unit (not shown) of a stapling device (not shown). Engagement of annular extension 120 of shipping cap 100 with knife carrier 52 of loading unit 10 prevents distal advancement of knife carrier 52, thereby ensuring knife carrier 52 is maintained in a proper position for alignment with a drive mechanism (not shown), or to an adapter assembly (not shown), of an actuation unit (not shown) or prior to and during attachment of loading unit 10 to the actuation unit or adapter assembly. Engagement of snap features 132, 142 of respective first and second arms 130, 140 of annular extension 120 of shipping cap 100 with ridges 28 formed on inner cylindrical portion 24 of housing 20 of loading unit 10 frictionally secures shipping cap 100 with loading unit 10.

Turning back to FIGS. 3 and 4, when shipping cap 100 is received on the distal end of loading unit 10, first and second legs 160, 170 of shipping cap 100 are received about, i.e., straddle, outer cylindrical portion 22 of housing 20 of loading unit 10 such that tabs 164, 174 of respective first and second legs 160, 170 are received within openings 25 formed in outer cylindrical portion 22 of housing 20 of loading unit 10 and within openings 35 of pusher adapter 32 of staple pusher assembly 30 of loading unit 10. When tabs 164, 174 of respective first and second legs 160, 170 of shipping cap 100 are received within openings 25 of outer cylindrical portion 22 of housing 20 of loading unit 10 and within openings 35 of pusher adapter 32 of staple pusher assembly 30 of loading unit 10, engagement of proximal facing surfaces 164a, 174a of tabs 164, 174, respectively, of respective first and second legs 160, 170, with pusher adapter 32, prevents distal advancement of pusher adapter 132. This ensures that pusher adapter 32 is maintained in a proper position for alignment with a drive mechanism (not shown) of an actuation unit (not shown) or adapter assembly (not shown) prior to and during attachment of loading unit 10 to the actuation unit.

As discussed above, shipping cap 100 remains secured to the distal end of loading unit 10 until loading unit 10 is secured to an actuation unit (not shown) of a stapling device (not shown) or an adapter assembly (not shown). Once loading unit 10 is properly secured to the actuation unit or the adapter assembly, the stapling device is either automatically or manually actuated to advance a retaining pin 60 (FIG. 11) of the stapling device to engage proximal surface 152 of ejection post 150 of shipping cap 100. Engagement of ejection post 150 by retaining pin or trocar tip 60 causes shipping cap 100 to be moved distally relative to loading unit 10. Distal movement of shipping cap 100 relative to loading unit 10 causes snap features 132, 142 of first and second arms 130, 140, respectively, of annular extension 120 of shipping cap 100 to disengage from ridges 28 of inner cylindrical portion 24 of housing 20 of loading unit 10, thereby releasing shipping cap 100 from engagement with loading unit 10 and permitting separation of shipping cap 100 from loading unit 10.

In one embodiment, loading unit 10 includes a chip, e.g., EPROM chip, configured to identify loading unit 10 to the actuation unit; to signal to the actuation unit that loading unit 10 includes shipping cap 100 and that loading unit 10 has been properly secured to the actuation unit; and to activate advancement of retaining pin 60 to separate shipping cap 100 from loading unit 10. In an alternative embodiment, once loading unit 10 is properly secured to the actuation unit, retaining pin 60 may be manually advanced by a user to separate shipping cap 100 from loading unit 10.

As described above, distal movement of shipping cap 100 relative to loading unit 10 causes withdrawal of tabs 164, 174 of respective first and second legs 160, 170 of shipping cap 100 from within openings 35 of pusher adapter 32 of staple pusher assembly 30 of loading unit 10 and from within openings 25 of outer cylindrical portion 22 of housing 20 of loading unit 10. Specifically, as shipping cap 100 is moved distally relative to loading unit 10, inclined surfaces 164b, 174b of tabs 164, 174, respectively, of respective first and second legs 160, 170 engage pusher adapter 32 and outer cylindrical portion 22 of housing 20 thereby causing first and second legs 160, 170 to flex radially outward. As first and second legs 160, 170 flex radially outward, tabs 164, 174 formed on proximal ends 162a, 172a, respectively, of respective first and second legs 160, 170 of shipping cap 100 are withdrawn from within openings 25, 35 of respective outer cylindrical portion 22 of housing 20 of loading unit 10 and pusher adapter 32 of stapler pusher assembly 30 of loading unit 10. Continued distal movement of shipping cap 100 causes separation of shipping cap 100 from loading unit 10. Once shipping cap 100 is separated from loading unit 10, the stapling device may be used in a traditional manner.

With reference now to FIGS. 12-15, a shipping member according to an alternative embodiment of the present disclosure is shown generally as shipping cap 200. Shipping cap 200 is substantially similar in structure and function to shipping cap 100 described hereinabove and will only be described as relates to the differences therebetween. Shipping cap 200 is configured to be selectively secured to loading unit 10.

Shipping cap 200 includes a base 210, an annular extension 220 extending proximally from base 210, and first and second legs 260, 270 extending proximally from base 210. Base 210 of shipping cap 200 is configured for atraumatic insertion into a lumen (not shown) of a patient (not shown). As shown, base 210 includes a substantially conical shape or outer profile having a rounded distal tip 210b. It is envisioned that base 210 may have other atraumatic configurations, e.g., hemispherical.

Base 210 defines at least one throughhole 211 therein. Throughhole 211 is configured to receive a suture (not shown), cord, or other means of retrieving shipping cap 200. The suture may be used to facilitate delivery or manipulation of loading unit 10 prior to attachment of loading unit 10 to an actuation unit; to facilitate separation of shipping cap 200 from loading unit 10; and/or to facilitate removal of shipping cap 200 from within a patient once shipping cap 200 is separated from loading unit 10.

In use, it is envisioned that shipping cap 200 is attached to the loading unit and will remain attached to loading unit 10 subsequent to attaching loading unit 10 to an actuation unit (not shown) of a stapling device (not shown) and will remain attached to loading unit 10 as loading unit 10 is positioned within the body of a patient.

As noted above, shipping cap 200 is configured to facilitate positioning of loading unit 10. In particular, the rounded conical shape of base 210 permits atraumatic insertion of loading unit 10 into, within, and/or through tissue of a patient. Once properly positioned, the stapling device may be operated in a manner described above to cause separation of shipping cap 200 from loading unit 10. Shipping cap 200 may then be removed from within the patient using the suture (not shown) attached to shipping cap 200 using throughhole 211 formed in base 210 of shipping cap 200 or by any other suitable means.

Figure 16:
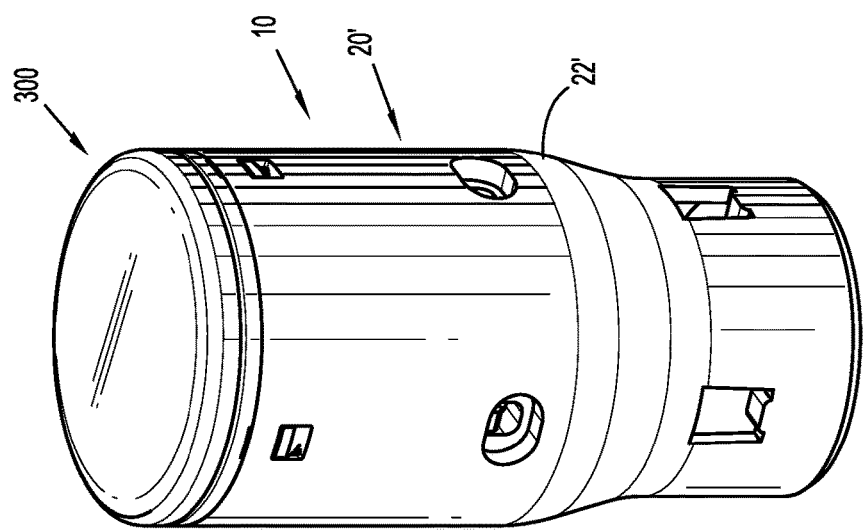
FIG. 16 is a perspective side view of a shipping member according to another embodiment of the present disclosure disposed on a replaceable loading unit.

With reference now to FIGS. 16-21, a shipping member according to another embodiment of the present disclosure is shown generally as shipping cap 300. Shipping cap 300 is configured for selective engagement with a loading unit 10' (FIG. 16). Shipping cap 300 and loading unit 10' are substantially similar in structure and function to shipping caps 100, 200 and loading unit 10, respectively, described hereinabove and will only be described as relates to the differences therebetween.

Figure 17:
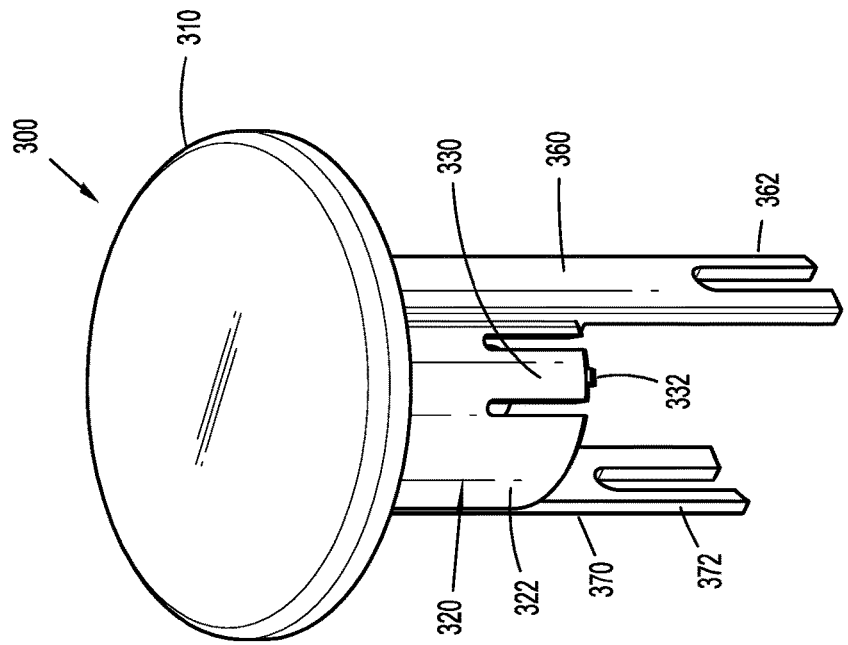
FIG. 17 is a perspective side view of the shipping member shown in FIG. 16.

With particular reference to FIGS. 17 and 18, shipping cap 300 includes a base 310, an annular extension 320 extending proximally from base 310, and first and second legs 360, 370 extending proximally from base 310, at a location radially inward of an outer terminal edge of base 310. An inner or staple retaining surface 312 of base 310 is formed radially outward of first and second legs 360, 370. Inner surface 312 of base 310 is configured to abut a staple cartridge 40' of loading unit 10' when shipping cap 300 is received on the distal end of loading unit 10' to maintain staples "S" within cartridge pockets 41' of staple cartridge 40'.

Annular extension 320 includes cylindrical body 322 and first and second arms 330, 340. Each of first and second arms 330, 340 includes a snap feature 332, 342 for selective frictional engagement with inner cylindrical portion 24' of housing 20' of loading unit 10'.

With reference still to FIGS. 17 and 18, first and second legs 360, 370 of shipping cap 300 extend proximally from opposite sides of annular extension 320 of shipping cap 300 and are configured to be received within loading unit 10'. In this manner, first and second legs 360, 370 contained with loading unit 10' and are protected from being contacted during shipping and attachment of loading unit 10', thereby preventing inadvertent separation of shipping cap 300 from loading unit 10'.

Although shown as being integrally formed with annular extension 320, is it envisioned that first and second legs 360, 370 of shipping cap 300 may be formed independently of annular extension 320. First and second legs 360, 370 of shipping cap 300 are radially offset from first and second arms 330, 340 of annular extension 320 of shipping cap 300 to permit flexion of first and second arms 330, 340.

Moreover, while being shown as having two legs formed on opposing sides of annular extension 320, it is envisioned that shipping cap 300 may include only a single leg or more than two legs and the legs may be radially disposed about annular extension 320 in any spacing. Each of first and second legs 360, 370 include a bifurcated free end 362, 372, respectively, configured for engaging pusher adapter 32' of staple pusher assembly 30' of loading unit 10'.

Although shown as being bifurcated, it is envisioned that free ends 362, 372 of first and second legs 360, 370, respectively, may form a solid member or be otherwise suitably configured for engagement with pusher adapter 32' of staple pusher assembly 30' of loading unit 10'. Engagement of first and second legs 360, 370 of shipping cap 300 with pusher adapter 32' of staple pusher assembly 30' of loading unit 10' prevents distal advancement of pusher adapter 32'.

Turning briefly to FIG. 19, knife carrier 52' of knife assembly 50' defines cutouts 55. Cutouts 55 correspond in size and location to first and second legs 360, 370 of shipping cap 300 and are configured to receive first and second legs 360, 370 of shipping cap 300 therethrough when shipping cap 300 is selectively secured to loading unit 10' (FIG. 16).

Figure 21:
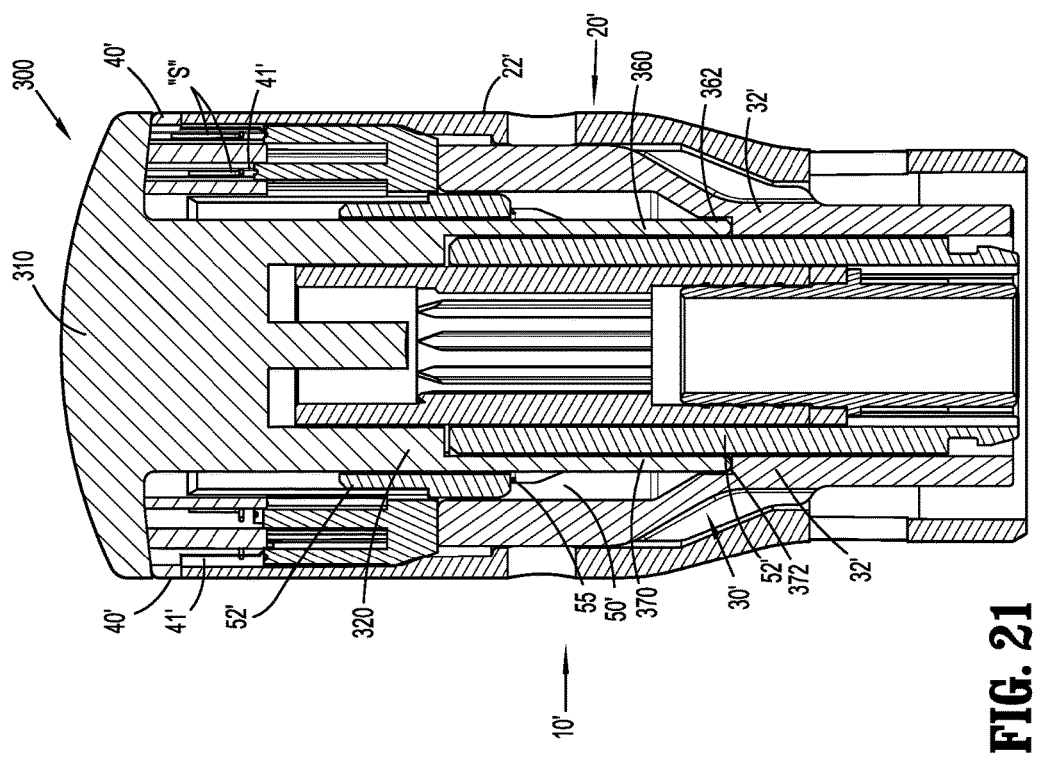
FIG. 21 is a cross-sectional side view of the shipping member and loading unit shown in FIG. 16.
Figure 20:
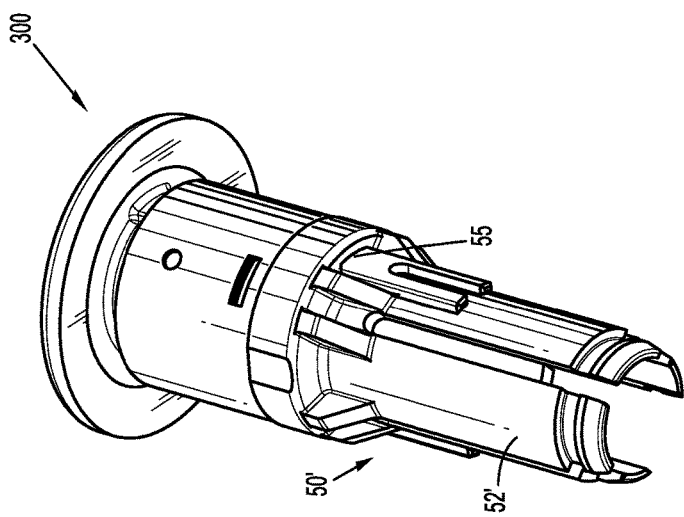
FIG. 20 is a perspective side view of the shipping member and knife assembly shown in FIG. 19, with the parts attached.

With reference now to FIGS. 20 and 21, shipping cap 300 is shown secured to loading unit 10'. In particular, annular extension 320 of shipping cap 300 is received between outer and inner cylindrical portions 22', 24' of housing 20' of loading unit 10' and about inner cylindrical portion 24' of housing 20'. A proximal end of annular extension 320 of shipping cap 300 engages knife carrier 52' of knife assembly 50', thereby preventing distal movement of knife carrier 52' prior to separation of shipping cap 300 from loading unit 10'. Free ends 362, 372 of respective first and second legs 360, 370 of shipping cap 300 engage pusher adapter 32' of staple pusher assembly 30' of loading unit 10', thereby preventing movement of pusher adapter 32' prior to separation of shipping cap 300 from loading unit 10'.

Figure 22:
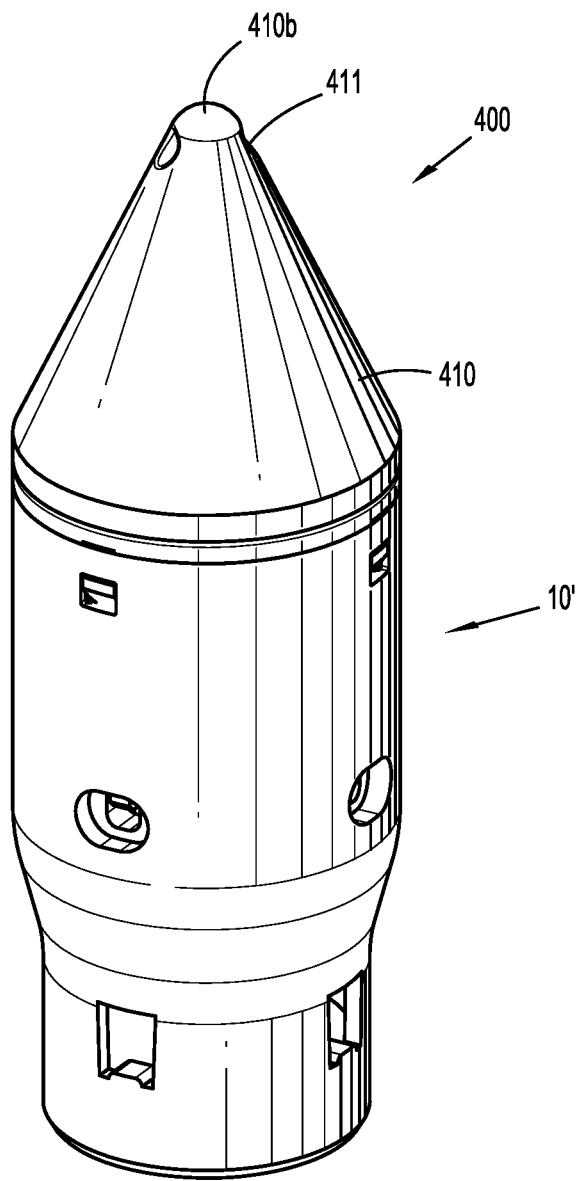
FIG. 22 is a perspective side view of shipping member according to yet another embodiment of the present disclosure disposed on a replaceable loading unit.
Figure 23:
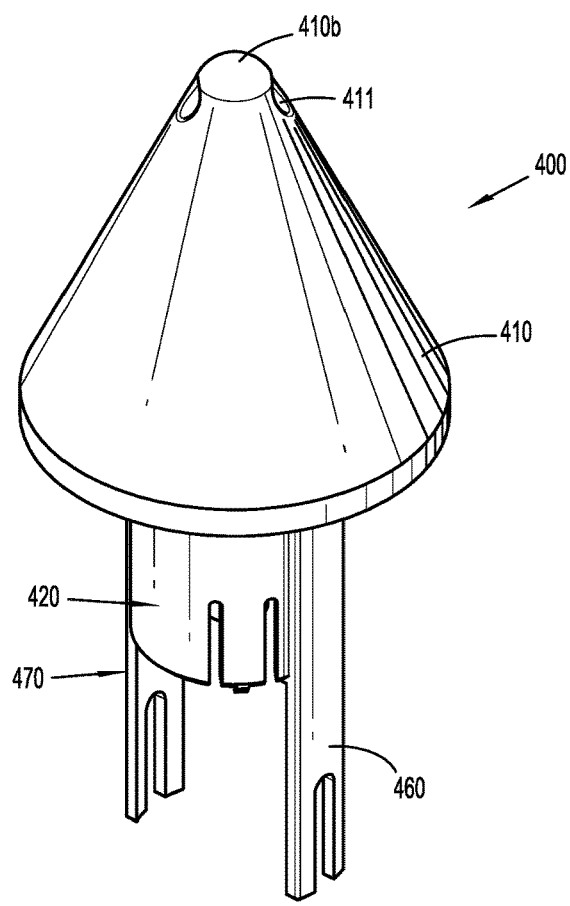
FIG. 23 is a perspective side view of the shipping member shown in FIG. 22.
Figure 24:
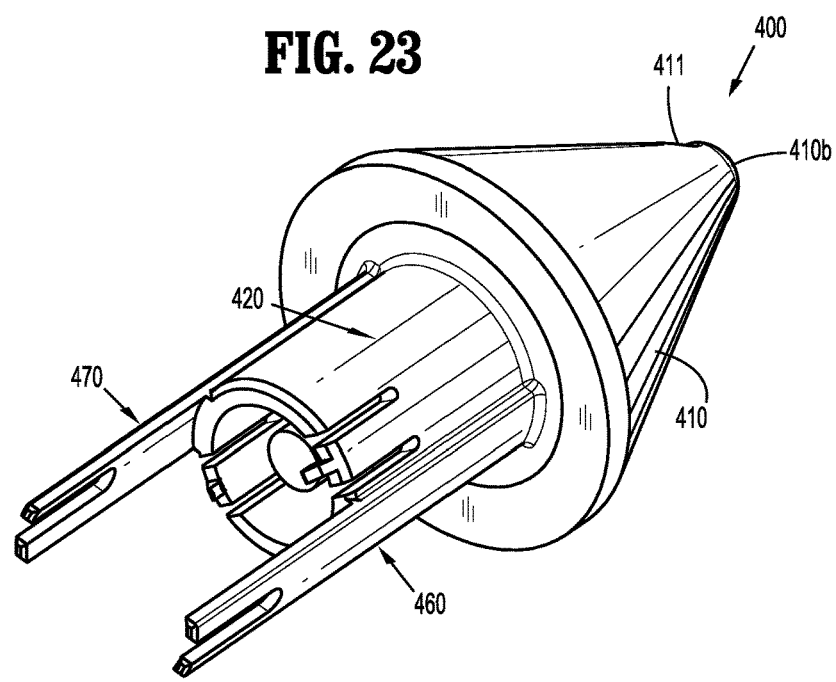
FIG. 24 is a perspective end view of the shipping member shown in FIG. 22.

With reference now to FIGS. 22-24, a shipping member according to still another embodiment of the present disclosure is shown generally as shipping cap 400. Shipping cap 400 is substantially similar in structure and function to shipping caps 200, 300 described hereinabove and will only be described as relates to the differences therebetween.

Shipping cap 400 includes a base 410, an annular extension 420 extending proximally from base 410, and first and second legs 460, 470 extending proximally from base 410. Base 410 of shipping cap 400 is configured for atraumatic insertion into a lumen (not shown) of a patient (not shown). As shown, base 410 includes a substantially conical shape or outer profile having a rounded distal tip 410b.

In each of the embodiments disclosed herein, the stapling apparatus can have surgical staples arranged in circular rows, rows having some other arcuate shape, linear or other shapes. In any of the embodiments disclosed herein the snap features may be replaced with other attachment features such as bayonet, latch, etc.

Base 210 defines a throughhole 411 therein. Throughhole 411 is configured to receive a suture (not shown), cord, or other means of retrieving shipping cap 400.

Although the illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure. For example, any of the shipping caps 100, 200, 300 or 400 can be used with a suture, as discussed above, and can include an opening or hole for the suture. The shipping cap can interact with a mechanism inside the stapling device, such as the trocar. The base of the shipping cap, in any of the embodiments disclosed herein, can be essentially flat, essentially conical or tapered, or curved/hemispherical.

What is claimed is:

1. A shipping cap for a loading unit of a circular stapler, the shipping cap comprising:

a base including an inner surface and an outer terminal edge;

an annular extension extending proximally from the base and configured for engagement by a knife assembly of a loading unit; and first and second legs disposed radially inward of the outer terminal edge of the base and extending proximally from the base.

2. The shipping cap of claim 1, wherein the inner surface is configured to be disposed adjacent a staple cartridge of a loading unit to maintain a plurality of staples within the staple cartridge.

3. The shipping cap of claim 1, wherein the inner surface is formed radially outward of the first and second legs.

4. The shipping cap of claim 1, wherein the annular extension includes a cylindrical body and first and second arms.

5. The shipping cap of claim 4, wherein each of the first and second arms includes a snap feature for selective frictional engagement with an inner cylindrical portion of a housing of a loading unit.

6. The shipping cap of claim 4, wherein the first and second legs are radially offset from the first and second arms.

7. The shipping cap of claim 1, wherein the first and second legs extend proximally from opposite sides of the annular extension.

8. The shipping cap of claim 1, wherein the first and second legs are configured to be received within the loading unit.

9. The shipping cap of claim 1, wherein the first and second legs are integrally formed with the annular extension.

10. The shipping cap of claim 1, wherein each of the first and second legs includes a bifurcated free end configured for engaging a pusher adapter of a staple pusher assembly of the loading unit.

11. The shipping cap of claim 1, wherein the first and second legs are configured to prevent distal advancement of a pusher adapter of a loading unit.

12. The shipping cap of claim 1, wherein the base includes a substantially conical shape.

13. The shipping cap of claim 12, wherein the base defines a throughbore.

14. The shipping cap of claim 1, wherein the base includes an outer profile having a rounded distal tip.

15. A loading unit for use with a circular stapler, the loading unit comprising:

a housing including outer and inner cylindrical portions;

a knife carrier operably disposed within the housing;

the shipping cap of claim 1 selectively secured relative to the housing, wherein the annular extension is received between the outer and inner cylindrical portions.

16. The loading unit of claim 15, wherein the knife carrier defines cutouts that receive the first and second legs of the shipping cap.

17. The loading unit of claim 15, wherein a proximal end of the annular extension of the shipping cap engages the knife carrier to prevent distal movement of the knife carrier.

18. The loading unit of claim 15, further comprising a pusher adapter operably disposed within the housing; wherein the first and second legs each include a free end, the free ends engaging the pusher adapter to prevent distal movement of the pusher adapter prior to separation of the shipping cap from the housing.

* * * * *